United States Patent
Watanabe et al.

(10) Patent No.: US 8,124,933 B2
(45) Date of Patent: Feb. 28, 2012

(54) MAPPING-PROJECTION-TYPE ELECTRON BEAM APPARATUS FOR INSPECTING SAMPLE BY USING ELECTRONS EMITTED FROM THE SAMPLE

(75) Inventors: Kenji Watanabe, Hiratsuka (JP); Takeshi Murakami, Tokyo (JP); Masahiro Hatakeyama, Fujisawa (JP); Yoshinao Hirabayashi, Matsumoto (JP); Tohru Satake, Chigasaki (JP); Nobuhara Noji, Zushi (JP); Yuichiro Yamazaki, Tokyo (JP); Ichirota Nagahama, Koga (JP)

(73) Assignees: Ebara Corporation, Tokyo (JP); Kabushiki Kaisha Toshiba, Tokyo (JP)

( * ) Notice: Subject to any disclaimer, the term of this patent is extended or adjusted under 35 U.S.C. 154(b) by 198 days.

(21) Appl. No.: 12/538,416

(22) Filed: Aug. 10, 2009

(65) Prior Publication Data
US 2010/0019149 A1    Jan. 28, 2010

Related U.S. Application Data

(62) Division of application No. 10/543,151, filed on Apr. 18, 2006, now Pat. No. 7,592,586.

(30) Foreign Application Priority Data

Jan. 27, 2003 (JP) ................ 2003-016987
Jan. 29, 2003 (JP) ................ 2003-020126

(51) Int. Cl.
    *H01J 37/26* (2006.01)
(52) U.S. Cl. .............. 250/310; 250/397
(58) Field of Classification Search ............ 250/310, 250/397
    See application file for complete search history.

(56) References Cited

U.S. PATENT DOCUMENTS
5,576,833 A    11/1996    Miyoshi et al.
(Continued)

FOREIGN PATENT DOCUMENTS
EP    0949653 A2    10/1999
(Continued)

OTHER PUBLICATIONS

Anonymous; "Electron Energy Discriminator for Wafer/Chip Testing", IBM Technical Disclosure Bulletin, vol. 23, No. 6, Nov. 1980, pp. 2288-2290.

(Continued)

*Primary Examiner* — Kiet Nguyen
(74) *Attorney, Agent, or Firm* — Westerman, Hattori, Daniels & Adrian, LLP

(57) ABSTRACT

An apparatus capable of detecting defects of a pattern on a sample with high accuracy and reliability and at a high throughput, and a semiconductor manufacturing method using the same are provided. The electron beam apparatus is a mapping-projection-type electron beam apparatus for observing or evaluating a surface of the sample by irradiating the sample with a primary electron beam and forming on a detector an image of reflected electrons emitted from the sample. An electron impact-type detector such as an electron impact-type CCD or an electron impact-type TDI is used as the detector for detecting the reflected electrons. The reflected electrons are selectively detected from an energy difference between the reflected electrons and secondary electrons emitted from the sample. To eliminate charge-up caused on the sample surface by irradiation with the primary electron beam, the surface of the sample is covered with a cover placed above the sample and a gas is supplied to the space above the sample covered with the cover. The gas is brought into contact with the sample surface to reduce charge-up on the sample surface.

8 Claims, 8 Drawing Sheets

U.S. PATENT DOCUMENTS

| | | | |
|---|---|---|---|
| 6,087,659 | A | 7/2000 | Adler et al. |
| 6,184,526 | B1 * | 2/2001 | Kohama et al. ............... 250/310 |
| 6,365,897 | B1 * | 4/2002 | Hamashima et al. ......... 250/310 |
| 6,465,795 | B1 | 10/2002 | Madonado et al. |
| 6,586,733 | B1 | 7/2003 | Veneklasen et al. |
| 6,979,822 | B1 | 12/2005 | Stewart et al. |
| 7,138,629 | B2 * | 11/2006 | Noji et al. ..................... 250/311 |

FOREIGN PATENT DOCUMENTS

| | | | |
|---|---|---|---|
| JP | 4242060 | A | 8/1992 |
| JP | 10-106472 | * | 4/1998 |
| JP | 2002141013 | A | 5/2002 |
| WO | 9946798 | A1 | 9/1999 |
| WO | 0072355 | A1 | 11/2000 |

OTHER PUBLICATIONS

Zhu W et al.; "Large current density from carbon nanotube field emitters"; Applied Physics Letters, American Institute of Physics. New York, US; vol. 75, No. 6; Aug. 9, 1999; pp. 873-875.

International Search Report mailed Aug. 6, 2004 in Corresponding International Application No. PCT/JP2004/000711.

K. Tsuno, "Simulation of a Wien filter as beam separator in a low energy microscope", pp. 127-140, Ultramicroscopy 55 (1994).

Office Action issued Jun. 10, 2009 in Corresponding Taiwanese Patent Application No. 093101710.

* cited by examiner

MAPPING-PROJECTION-TYPE ELECTRON BEAM APPARATUS FOR INSPECTING SAMPLE BY USING ELECTRONS EMITTED FROM THE SAMPLE

This application is a division of application Ser. No. 10/543,151 filed Apr. 18, 2006, which is hereby incorporated by reference in its entirety.

TECHNICAL FIELD

The present invention relates to an electron beam apparatus for performing inspection, observation and evaluation (electron beam testing) of the structure, electrical conduction, etc., of a sample surface by irradiating the sample surface with an electron beam and to an apparatus and method for inspecting defects on a pattern having a minimum line width of, for example, 0.15 μm or less with high accuracy and reliability and at a high throughput.

BACKGROUND ART

An inspection apparatus is known wherein a defect existing in a wafer is detected in such a manner that secondary electrons emitted when the surface of the substrate is irradiated and scanned with an electron beam are detected, wherein a wafer image data is produced on the basis of the detection result, and wherein the image data on each die on the wafer and the adjacent image data are compared with each other. A mapping-projection-type inspection apparatus is also well-known which obtains data on an image on a wafer in such a manner that the substrate is irradiated with a primary electron beam and secondary electrons emitted from the substrate are imaged by a secondary lens system.

The mapping-projection-type inspection apparatus is capable of irradiating a large area at a time. Therefore, such a system can have the number of scanning times markedly reduced and enables evaluation and observation of a sample at a higher throughput in comparison with the SEM system. An electron beam apparatus such as the mapping-projection-type inspection apparatus obtains an observed image by imaging, on a detector, through a mapping projection system, secondary electrons emitted from a sample. However, such a beam apparatus has a problem that the secondary electrons have a comparatively small energy of about several electron volts in the vicinity of the sample and therefore drift at the time of imaging under the influence of a surface potential difference due to charging, i.e., a potential difference caused by wiring conductors or the like and an insulating material existing between the wiring conductors, and a distortion in the observed image results.

On the other hand, reflected electrons, i.e., electrons reflected by the sample irradiated with the electron beam, have substantially the same energy as the incident energy, i.e., an energy of 2 to 3 keV, which is about 100 times higher than that of secondary electrons. For this reason, if reflected electrons are imaged by a mapping projection system, an observed image can be obtained which is not easily influenced by a surface potential difference and which has only a limited image distortion. However, the emission ratio of reflected electrons is much lower than that of secondary electrons. Therefore there is a problem that, in the case of detection of reflected electrons using a conventional detection system, e.g., one based on a combination of an MCP, a fluorescent screen and a CCD, the S/N ratio is not sufficiently high, it is necessary to increase an amount of electron beam current and a MCP gain, and, therefore, the electron source and the MCP are deteriorated in a short time period.

As regards secondary electrons, a primary electron beam irradiation energy and an efficiency σ of emission of secondary electrons, for example, in the case of irradiating an insulating material made of $SiO_2$ with a primary electron beam are in a relationship shown in FIG. 1. As shown in the figure, when the irradiation electron energy is in the range from a lower limit of about 50 eV to an upper limit of 1500 to 2000 eV, the secondary electron emission efficiency σ is 1 or higher and more secondary electrons than the incident primary electrons are emitted. Therefore, the insulating material surface is positively charged up. When the irradiation electron energy is out of the above-described range, the secondary electron emission efficiency σ is lower than 1 and, therefore, the insulating material surface is negatively charged up.

If such charge-up is increased, a distortion is caused in an image formed by secondary electrons for observation and evaluation. In the case of defect inspection, for example, by comparison between images of adjacent dies formed on a device wafer, therefore, there is a defect misdetection problem, i.e., a problem that a false defect detection result is obtained.

As regards negative charge-up, a method has been proposed in which a capillary tube is used to locally supply a gas to an observation position on a sample whereby gas molecules collide with the sample surface and become ions by coupling with electrons to neutralize electric charge on the sample surface. However, such a method cannot supply a gas uniformly to the entire sample surface in the mapping-projection-type electron beam apparatus that radiates a beam through a wide area, and is not suitable for the mapping-projection-type electron beam apparatus.

As regards positive charge-up, a method is conceivable in which a sample is irradiated with electrons by a hot filament-type electron source such as tungsten to neutralize the charge-up. In such a case, however, the insulating material changes easily from a positively charged state to a charge-zero state and, further, to a negatively charged state. Such a transition is difficult to control.

DISCLOSURE OF THE INVENTION

If a high-sensitivity electron-bombardment-type CCD (hereinafter referred to as "EB-CCD") in particular is used as a reflected electron detector, an S/N ratio can be improved while an amount of current and an MCP gain are maintained at the same levels as in the case of the conventional art. Also, a high-sensitivity image free from multiplication fluctuations caused in the case of using the conventional MCP can be obtained. Further, since a multiplication gain of the EB-CCD is determined by the energy incident on the CCD, it is possible to selectively take out reflected electrons by utilizing an energy difference between secondary electrons and reflected electrons if the EB-CCD is used.

Therefore, an object of the present invention is to provide, on the basis of the above-described knowledge, an electron beam apparatus capable of inspecting defects of a pattern with high accuracy and reliability and at a high throughput to solve the problems of the conventional detection apparatuses.

Another object of the present invention is to provide an electron beam apparatus arranged so as to be capable of observation and evaluation of the surface of a sample and detection of defects on the surface in such a state that there is no charge-up on the entire sample surface.

Further, still another object of the present invention is to provide a semiconductor device manufacturing method using such an electron beam apparatus.

To achieve the above-described objects, according to one aspect of the present invention, there is provided a mapping-projection-type electron beam apparatus for observing or evaluating a surface of a sample by irradiating the sample with a primary electron beam and imaging on a detector reflected electrons emitted from the sample, the apparatus having an electron-bombardment-type detector such as an electron-bombardment-type CCD or an electron-bombardment-type TDI as the detector for detecting the reflected electrons, the reflected electrons being selectively detected from the energy difference between the reflected electrons and secondary electrons emitted from the sample.

Preferably, an image processing mechanism which performs image processing on an output from the electron-bombardment-type detector to output an image for evaluation and inspection is further provided and a gain of the electron-bombardment-type detector and an amount of exposure of the image for evaluation and inspection are adjusted by changing the energy of the primary electron beam incident on the sample.

Preferably, the energy of the primary electron beam incident on the sample is set to 2 to 4 keV and the surface of the sample is thereby charged negatively to reduce image distortion due to charge-up on the surface of the sample.

Preferably, a landing energy of the primary electron beam on the sample is set to 0.2 to 4.0 kV and reflected electrons and backscattered electrons are thereby detected to improve the S/N ratio.

Preferably, cooling means for cooling the electron-bombardment-type detector to reduce heat generation due to electron bombardment is further provided.

According to another aspect of the present invention, there is provided an electron beam apparatus which irradiates a sample surface placed in a sample chamber with a primary electron beam and evaluates the sample surface on the basis of a secondary electron beam from the sample surface, the apparatus having means for supplying a gas so as to uniformly cover the whole sample surface, thereby reducing charge-up on the sample surface by contact between the sample surface and the gas.

The electron beam apparatus is capable of uniformly reducing charge-up caused on the sample surface by means of the gas uniformly supplied. More specifically, the sample is mounted on a stage set in the sample chamber and the means for supplying the gas has a cover which covers the sample mounted on the stage. At least one gas inlet is provided in the cover, and the gas is supplied through the gas inlet to a space surrounded by the cover above the sample. The sample surface, preferably the entire sample surface is thereby covered uniformly with the gas to reduce charge-up.

Further specifically, as a primary electron source for generating the primary electron beam, an electron source which irradiates the sample surface with electrons is provided. The sample surface is negatively or positively charged up according to the secondary electron emission rate. In either case, the sample surface may be first set in a negatively charged state by electron irradiation from the electron source, and the charged state may be neutralized by the gas. The electron source provided separately from the primary electron source radiates electrons at an electron energy of 2 to 4 keV. Preferably, the electron source is a carbon nanotube type of cold cathode electron source.

According to still another aspect of the present invention, there is provided a sample evaluation method in which a sample surface is irradiated with a primary electron beam and the sample surface is observed and evaluated on the basis of a secondary electron beam from the sample surface, the method including the steps of supplying a gas so as to uniformly cover the sample surface to neutralize the sample surface negatively charged up, and setting the pressure of the gas to 0.01 to 0.1 Pa. At such gas pressure, the sample surface can be suitably neutralized.

Preferably, the gas introduced into the sample chamber is one of nitrogen, water vapor, a halogen gas having high affinity to electrons, and one of chemical compounds thereof. Further, the above method may comprise the steps of preparing an electron source other than a generation source for the primary electron beam; irradiating the sample with electrons from the electron source; charging up the sample surface negatively; neutralizing the charge-up by the gas; and thereafter performing observation and evaluation of the sample surface by means of the primary electron beam.

According to the present invention, there is further provided a semiconductor device manufacturing method including a step of performing wafer evaluation at an intermediate stage in the process by using the above-described electron beam apparatus and method. This semiconductor manufacturing method ensures that a semiconductor device can be manufactured with markedly high efficiency while performing suitable wafer evaluation without being influenced by charge-up caused on the sample surface.

These and other objects and features of the present invention will be more clearly understandable through reading of the following detailed description with reference to the accompanying drawings.

BEST MODE FOR CARRYING OUT THE INVENTION

Figure 1:
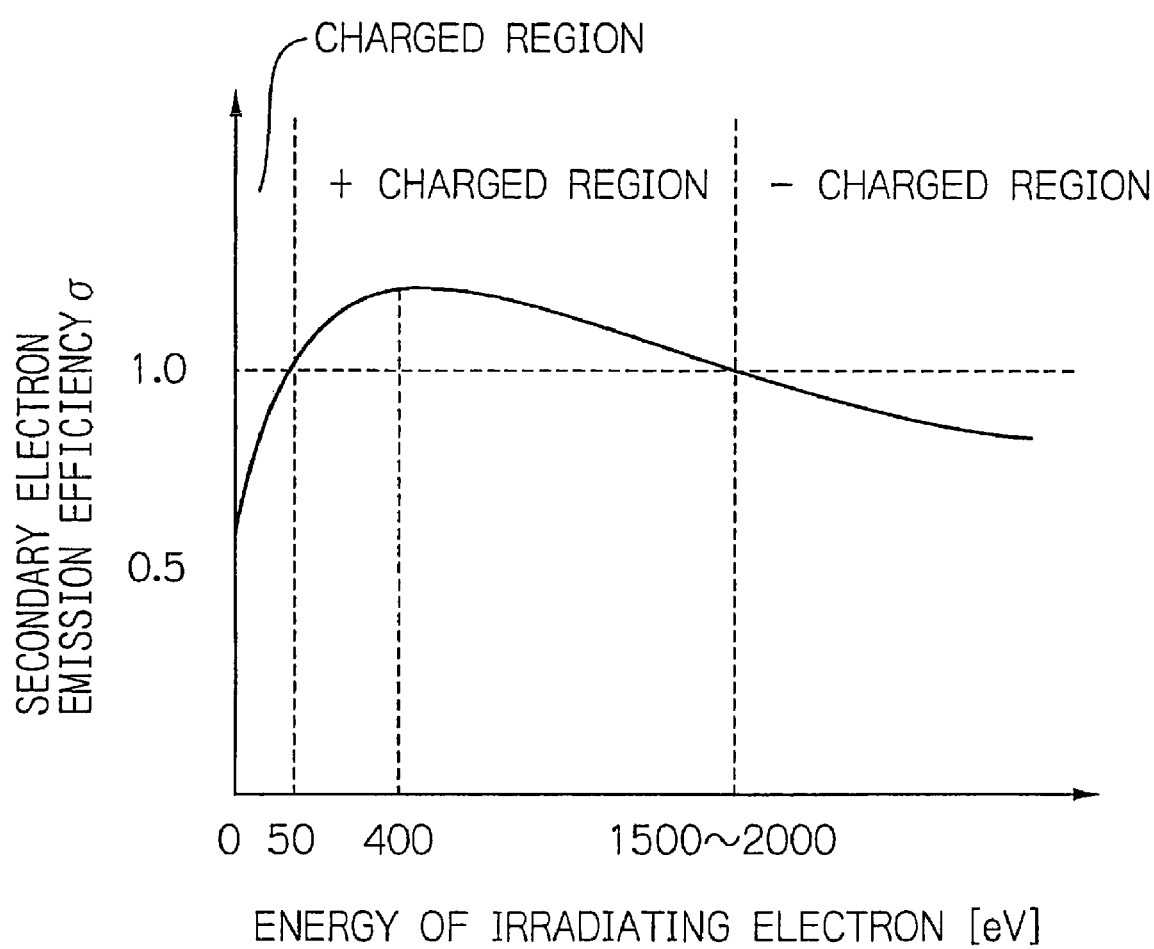
FIG. 1 is a diagram showing a relationship between energy of irradiation electrons and a secondary electron emission efficiency of an insulating material.

Embodiments of an electron beam apparatus in accordance with the present invention will be described below. It is noted that the present invention is not limited to the embodiments described below. In the drawings, like components are designated by the same reference numerals.

In one embodiment of the electron beam apparatus in accordance with the present invention, a high-sensitivity EB-CCD or an electron-bombardment-type time delayed integration (TDI) apparatus (hereinafter referred to as "EB-TDI") is used as a reflected electron detector in the conventional mapping-projection-type electron beam apparatus. Reflected electrons emitted from a sample substrate when the substrate is irradiated with a primary electron beam are imaged on such a detector in the secondary optical system as an EB-CCD under mapping-projection optical conditions.

Figure 2:
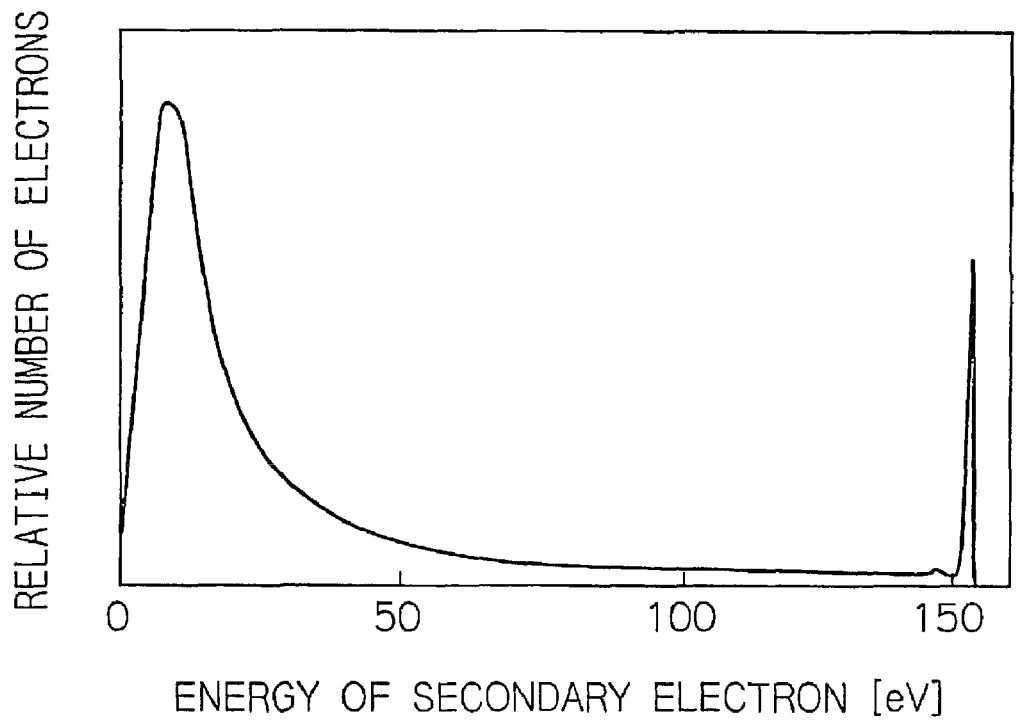
FIG. 2 is a diagram showing an energy distribution of emitted secondary electrons.

FIG. 2 is a graph showing a characteristic relating to energy of electrons emitted from an Au substrate and an emission coefficient when the Au substrate is irradiated with a primary electron beam at an incident energy of 155 eV (c.f.: "K. Ura Electron Beam Interaction with Sample" edited by John T. L. Thong, Electron Beam Technology, p. 180, Plenum Press, New York, 1993). According to this graph, the energy of secondary electrons by irradiation of electrons is distributed generally from 0 to 50 eV and almost all the secondary electrons have an energy of several electron volts when the substrate potential is the earth potential. On the other hand, reflected electrons have a peak of its energy distribution in the vicinity of 155 eV, substantially equal to that of the incident electrons. Therefore, the secondary electrons emitted from the sample move at low speed, exist in the vicinity of the sample and are influenced by the surface potential at the time of charging of the sample. In contrast, the reflected electrons have substantially the same energy as the energy of the incident electrons. For this reason, by using the reflected electrons, a sample image can be obtained without any influence by the surface potential of the substrate electrons and having no distortion.

In the case of imaging the secondary electrons emitted from the sample substrate, all the electrons having their energy distributed in the range from 0 to 50 eV are used. In contrast, in the case of using the reflected electrons emitted from the sample substrate, only the electrons corresponding to the energy peak of the incident electrons are used as described above and, therefore, an S/N ratio is not sufficiently high. To overcome this problem, the reflected electrons is detected by using a high-sensitivity EB-CCD or EB-TDI.

Figure 3:
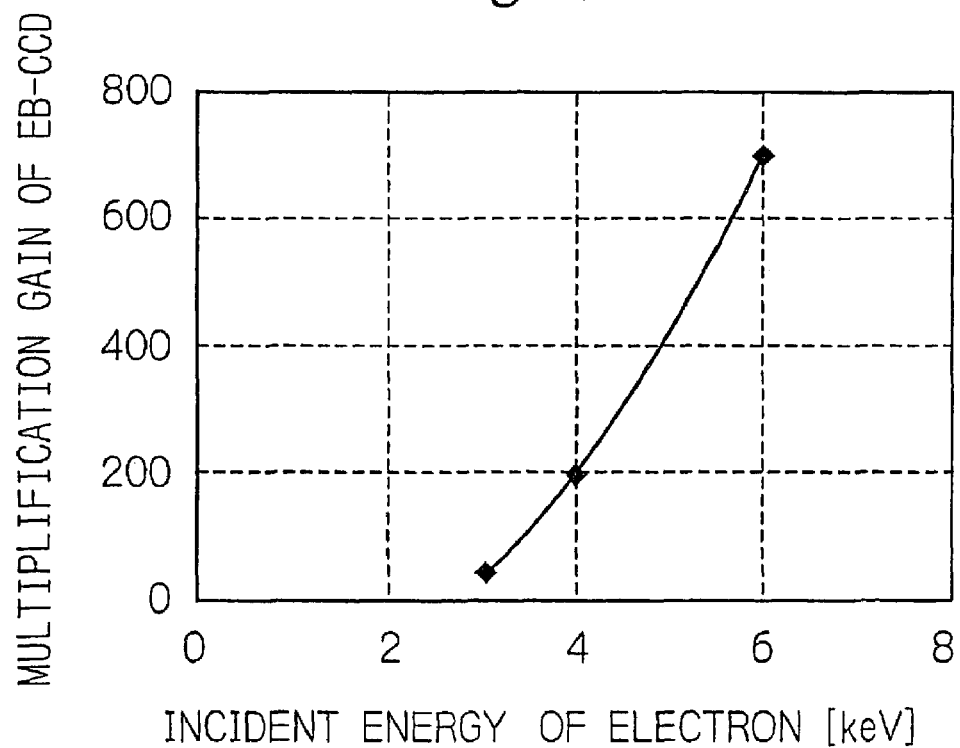
FIG. 3 is a diagram showing a relationship between incident energy of electrons and a multiplication gain of an EB-CCD.

FIG. 3 is a graph showing a multiplication gain of an EB-CCD with respect to incident energy of electrons. Since the energy of reflected electrons incident on the EB-CCD is 4 keV, the reflected electron multiplication gain is about 200 according to the graph of FIG. 3. In contrast, the secondary electrons, having energy of several electron volts, are not multiplied and therefore not detected. Consequently, only the reflected electrons can be detected. If an EB-TDI is used as a detector and a stage on which the sample substrate is mounted is continuously moved, consecutive images of a sample can be formed. The images thus formed enable observation and evaluation of the sample.

Figure 4:
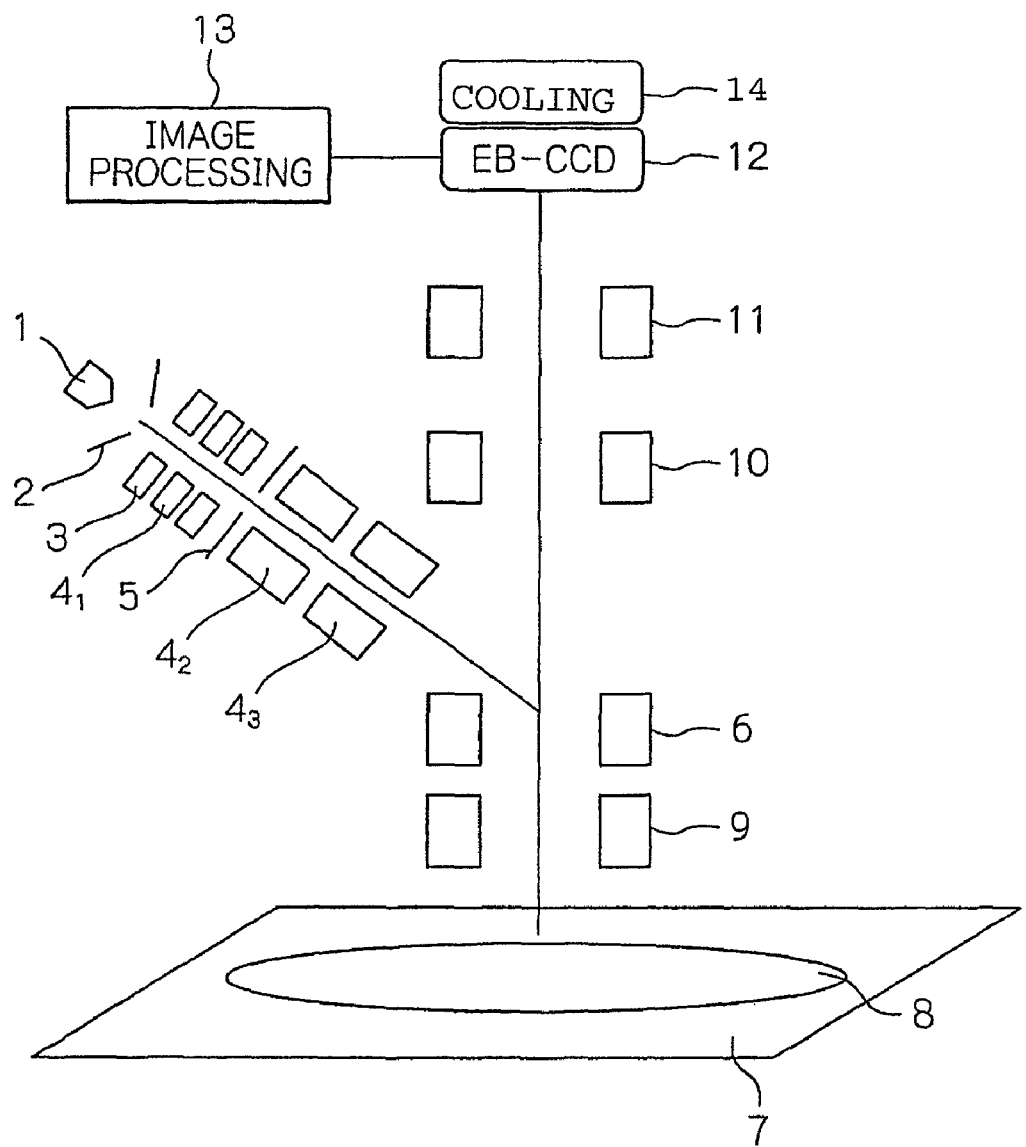
FIG. 4 is a diagram schematically showing an embodiment of a mapping-projection-type electron beam apparatus according to the present invention.

FIG. 4 schematically shows the construction of one embodiment of a mapping-projection-type electron beam apparatus according to the present invention. Referring to the figure, an electron beam emitted from an electron source 1 passes a Wehnelt electrode 2, an anode (acceleration electrode) 3, an electrostatic lens $4_1$ and an aperture (or a square opening) 5, further passes two electrostatic lenses $4_2$ and $4_3$ and enter an E×B filter 6. The Wehnelt electrode 2, the anode 3, the electrostatic lens $4_1$, the aperture 5, the electrostatic lenses $4_2$ and $4_3$ and the E×B filter 6 form a primary electron optical system.

In the E×B filter 6, the direction of travel of the electron beam is deflected by the action of electric and magnetic fields to irradiate a grounded wafer 8 having a size of, for example, 8 to 12 inches and placed on an X-Y-θ stage 7. The energy of the electron beam at this case is 2 to 4 keV, preferably about 4 keV. Circuit patterns for manufacturing, for example, an LSI are formed on the surface of the wafer 8.

When irradiated with the electron beam, reflected electrons having substantially the same energy as the energy of the incident electrons are emitted from the surface of the wafer 8. The reflected electrons are enlarged by 50 to 500 times by several electrostatic lens such as a single-stage electrostatic lens 9, a two-stage electrostatic lens 10 and a three-stage electrostatic lens 11 of a secondary electron optical system and form an image on a high-sensitivity EB-CCD 12. Since the wafer 8 has the ground potential and no retarding potential is applied to the wafer 8, the secondary electrons emitted from the wafer 8 do not enter secondary electron optical system. Also, since the EB-CCD 12 has a multiplication gain characteristic, as described above with reference to FIG. 3, the reflected electrons can be selectively detected by the EB-CCD 12.

If the electron beam apparatus shown in FIG. 4 is used as an apparatus for inspecting detects of a pattern formed on a wafer, a CCD image output from the EB-CCD 12 is supplied to and processed by an image processing system 13. The processed image is used to determine existence/nonexistence of defects on the pattern of the wafer and classify and identify the defects. For example, in the case of a wafer in an LSI manufacturing process, defective portions are detected by comparison between structures in cells or comparison in structures between dies. Further, data on portions on which such defect inspection has been performed and portions where defects have been detected may be stored, and the detected defects may be classified and identified to be fed back to for management of manufacturing steps.

Since the gain of the EB-CCD 12 is determined by the energy of incident electrons as shown in FIG. 3, an amount of exposure of the CCD image can be adjusted by changing the energy of the primary electrons incident on the wafer 8, when reflected electrons are detected. Also, a cooling mechanism 14 such as a Peltier element may be provided on the EB-CCD 12 to reduce heat generated by the incident beam impinging on the EB-CCD 12.

As described above with reference to FIG. 1, in the range in which the secondary electron emission efficiency σ is lower than 1, the surface of an insulating material is negatively charged since the number of secondary electrons is smaller than that of incident electrons emitted. In the case of the electron beam apparatus shown in FIG. 4, therefore, the surface of the wafer 8 is negatively charged if the electrons emitted from the electron source 1 have energy of 1.5 to 2.0 ke at the time of incidence on the wafer 8. Thus, an image for observation and/or evaluation which has a limited charge-up distortion can be obtained.

When experiments are conducted on an apparatus to which an electron beam apparatus as shown in FIG. 4 is embodied, it has been revealed that the efficiency of detection of reflected electron is increased and an image for observation and/or evaluation having a high S/N ratio can be obtained when the potential of the wafer 8, i.e., the landing energy of the primary electron beam is set in a range from −0.5 to −3 keV, in particular, to −2 keV.

The high-sensitivity EB-CCD 12 is used in the electron beam apparatus shown in FIG. 4. In place of the EB-CCD 12, a high-sensitivity EB-TDI may be used. In the case where the EB-TDI is used, the wafer 8 is not grounded, and, for example, the electron source 1 is set at a potential of −4 kV and the wafer 8 is set at a potential of −2 kV. As a result, the energy of electrons incident on the wafer 8 is set to 2 kV and reflected electrons having energy of 2 kV corresponding to the energy of the incident electrons can be produced. The reflected electrons are enlarged by 50 to 500 times and form an image on the EB-TDI, as described above with reference to FIG. 4. On the other hand, since the secondary electrons emitted from the wafer 8, having only energy of several electron volts, are filtered under conditions preset to the E×B filter 6, the aperture 5 and the electrostatic lens 9, the secondary electrons do not form any image on the surface of the EB-TDI. The above-described conditions are such as shown below:

Electric Field of E×B filter 6: 1937 V,
Magnetic Field of E×B filter 6: 111.8 mA,
Diameter of aperture 5: 65 μm,
Electrostatic lens 9: −1436 V,
Electrostatic lens 10: −322 V, and
Electrostatic lens 11: −499 V.

In the electron beam apparatus using the EB-TDI, the wafer 8 can be photographed continuously by irradiating the wafer 8 with an electron beam while the stage 7 on which the wafer 8 is mounted is continuously moved. An example of concrete operating conditions for this image pickup is in the following:

Stage 7 moving speed: 10 to 100 mm/sec.
Number of EB-TDI pixels: 4096×512 (i.e., accumulation at 512 stages)
Line frequency: 200 to 500 kHz
Minimum resolution: 30 to 100 nm.

When the electron beam apparatus capable of such consecutive image pickup is used, images can be picked up by step and repeat. Therefore, image pickup at higher speed can be performed to achieve a higher throughput in comparison with the case of using the EB-CCD. For example, the inspection time was three hours, when continuous image pickup from an 8-inch wafer having pixels each having a size of 50×50 nm resolvable by the secondary optical system was performed by setting the stage moving speed to 15 mm/sec. and the line frequency to 300 kHz.

Figure 5:
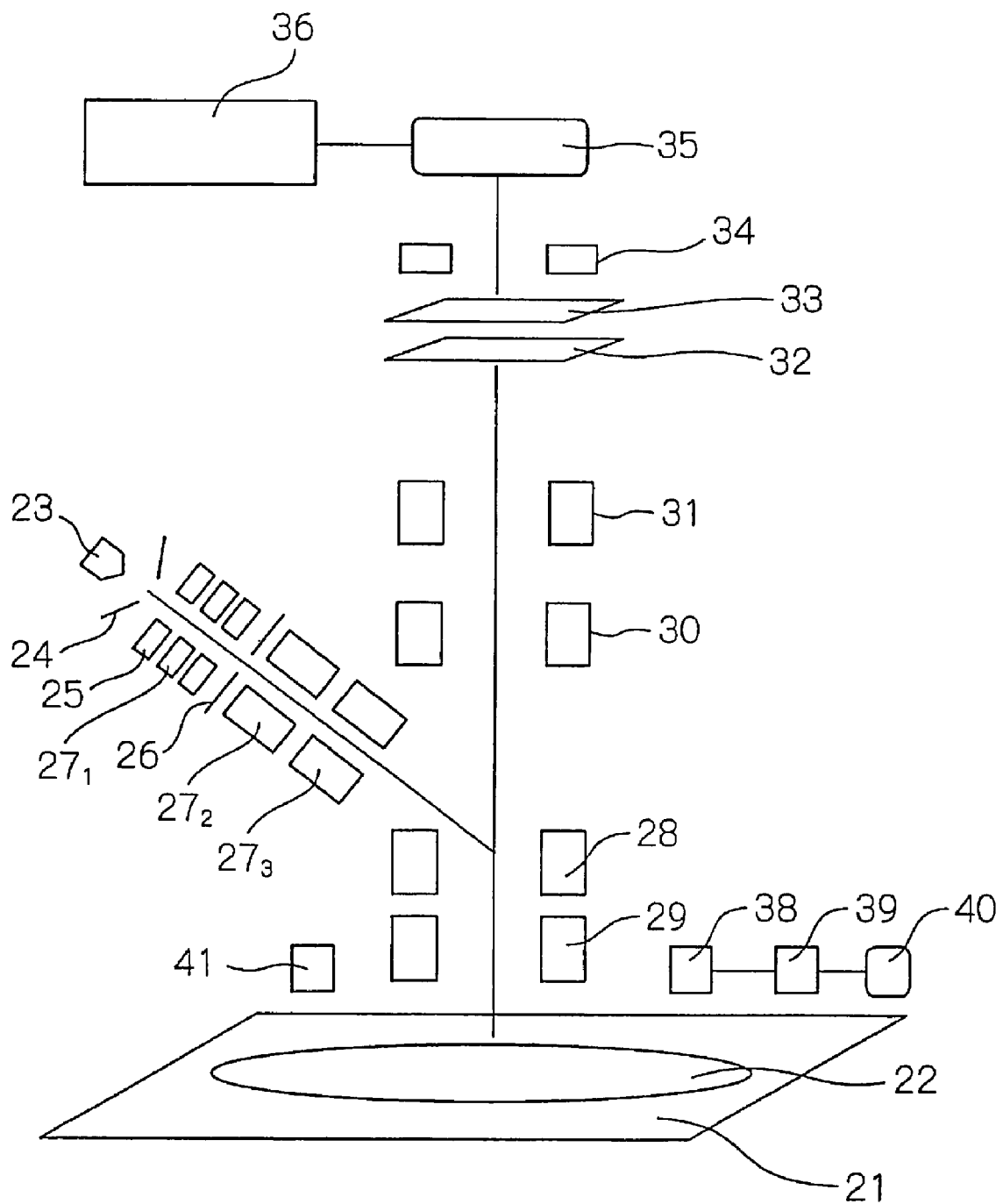
FIG. 5 is a diagram schematically showing the construction of another embodiment of the present invention.

FIG. 5 shows another embodiment of a mapping-projection-type electron beam apparatus according to the present invention. This apparatus has an (X-Y-θ) stage 21 on which a sample, e.g., an 8 to 12-inch silicon wafer 22 is mounted, a circuit pattern during an LSI manufacturing process being formed on the wafer. The sample 22 is irradiated through a primary electron optical system with a primary electron beam emitted from an electron source 23. The primary electron optical system has a Wehnelt electrode 24, an anode 25, electrostatic lenses 27₁, 27₂, and 27₃, and a beam splitter 28 such as an E×B filter. BY the primary electron irradiation, secondary electrons are generated from the surface of the sample 22. The secondary electrons emitted from the sample surface form a image on a detector through a secondary electron optical system. The secondary electron optical system has electrostatic lenses 29, 30, and 31 in a mapping optical system. The secondary electrons are enlarged by 50 to 500 times by these electrostatic lenses and enter the detector described below.

The detector has a microchannel plate (MCP) 32, a fluorescent screen 33, a relay lens 34, and a TDI (time delayed integration) 35. Secondary electrons reaching the detector are multiplied by the MCP 32 and converted into an optical signal by the fluorescent screen 33. The converted two-dimensional optical signal is guided to the TDI 35 by the relay lens 34 to be detected as an image.

Since the sample 22 is continuously moved, the two-dimensional signal can be obtained at high speed by the TDI 35. An image processing unit 36 receives the signal output from the TDI 35 and forms an electrical file of the sample 22, detects defects in the sample 22 by using the image and classifies and identifies the detected defects.

Information thus obtained is fed back to the manufacturing management.

When an amount of the secondary electrons emitted from such a sample 22 as a wafer is smaller than an amount of the primary electrons radiated to the sample 22, that is, the secondary electron emission efficiency δ is equal to or less than none, negative charge-up occurs on the surface of the sample 22, particularly portions made of an insulating material. Therefore, there is a possibility of occurrence of distortion in an image for observation and evaluation formed by using the secondary electrons. Conversely, when the secondary electron emission efficiency δ is equal to or higher than one, the surface of the sample 22 is positively charged up and there is a possibility of the same problem as that in the case of the negative charge-up.

Figure 6:
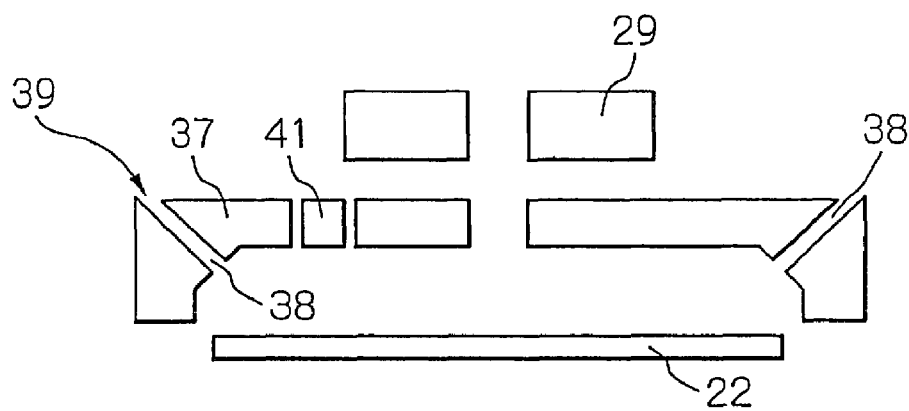
FIG. 6 is a cross-sectional view of a sample and a cover covering the sample in the apparatus shown in FIG. 5.

To eliminate such charge-up, the embodiment shown in FIG. 5 is provided with such means as described below. To cope with negative charge-up, a cover 37 is provided so as to cover the entire region of the sample 22 mounted on the stage 21, as shown in FIG. 6. A gas inlet 38 is formed in the cover 37. As shown in FIG. 5, a nitrogen tank 40 is connected to the gas inlet 38 via a flow rate controller 39. In order to uniformly eliminate charge-up on the entire surface of the sample 22, it is important to introduce a nitrogen gas into the cover 37 as uniformly as possible. To do this, a plurality of gas inlets 38, preferably eight gas inlets 38, are provided at equal intervals in a peripheral portion of the cover 37. The diameter of each gas inlet 38 is about 1 mm. Nitrogen molecules of the nitrogen gas introduced into the cover 37 through the gas inlets 38 impinge on the surface of the sample 22 and neutralize negative charge on the surface of the sample 22.

It is noted that a gas to be brought into contact with the surface of the sample 22 is not limited to nitrogen. Water vapor, a halogen gas having high affinity to electrons or a chemical compound thereof can be used. Thus, the sample 22 is neutralized from a negatively charged state to a zero charge state and is observed and evaluated with the primary electron beam while keeping the neutralized state.

If the secondary electron emission efficiency 6 is equal to or higher than one and the sample is positively charged up, a hot electron source 41 having a tungsten filament is provided, for the purpose of avoiding the positive charge-up, at a position above the stage 21 as shown in FIG. 5 or to form a part of the cover 37 as shown in FIG. 6. The hot electron source 41 radiates hot electrons to the surface of the sample 22 positively charged up. The positively charged state on the surface of the sample 22 is thus neutralized. Ordinarily, it is difficult to neutralize charge-up by hot electrons in a controlled state. Therefore the cover 37 may be provided as shown in FIG. 6 to bring a gas into contact with the sample 22. This enables a state of electric charge on the surface of the sample 22 to be balanced without depending on how much amount the hot electron source 41 irradiates or how long the sample 22 is radiated. Thus, the sample 22 can be observed and evaluated in a non-charged-up state.

Example 1

Figure 7:
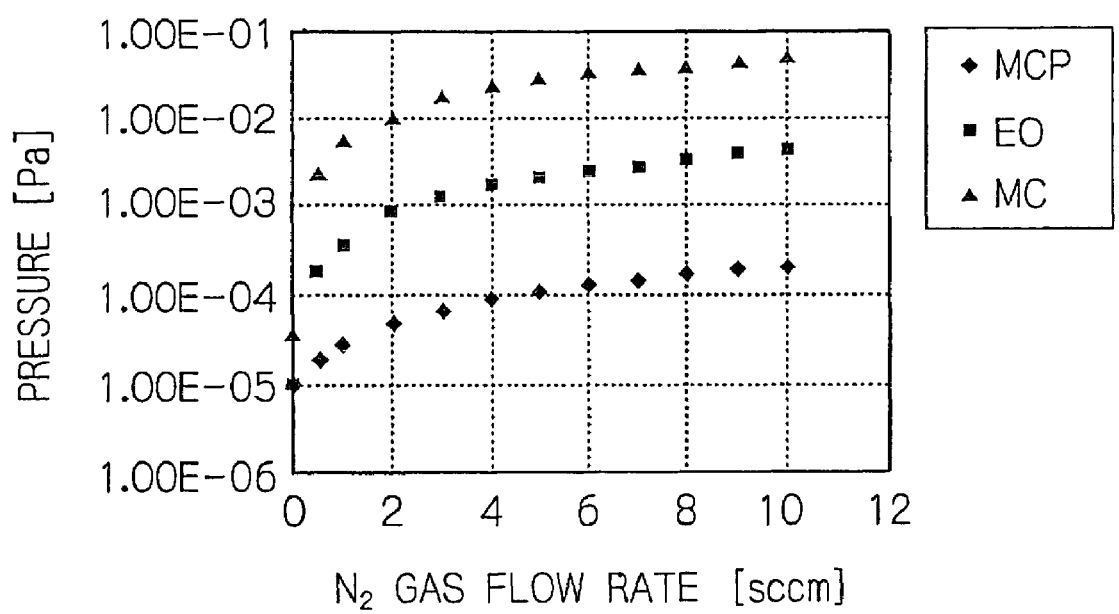
FIG. 7 is a graph showing a flow rate of a gas introduced into a sample chamber of the electron beam apparatus as well as pressures within chambers including the sample chamber.

The entire sample chamber was evacuated with a turbomolecular pump to about 1.0 E-5 Pa. A nitrogen gas was thereafter introduced from the nitrogen tank 40 into the cover 37 through the gas inlets 38 after reducing the pressure of the nitrogen gas to about 0.1 MPa by means of a regulator and adjusting a flow rate to 5 sccm with the flow rate controller 39. The introduced gas increased the pressure in the cover 37 to 4.0 E-2 Pa, but such containers, for example, the electron gun chamber and the detector, that require high vacuum environment were maintained in a high vacuum state such as shown in FIG. 7 by a differential evacuation mechanism. In FIG. 7, MC indicates the gas pressure in the cover 37, EO indicates the gas pressure in the electron optical system chamber including E×B 28, MCP indicates the pressure in the chamber containing the detector including the MCP 32 and fluorescent screen 33.

Under such a pressure condition, the hot electron source 41 having a tungsten filament irradiates, for about one second, an area of 20×20 mm just below the hot electron source 41 in advance with hot electrons having an incident energy of 3 kV and a current density of 1.0 E-4 A/cm$^2$. Subsequently, a nitrogen gas is used to neutralize the wafer for about three seconds. Thereafter, the area irradiated with the hot electrons is moved to a position where the wafer is irradiated with the primary electron beam and then is irradiated with primary electrons at an energy of 3 keV. Secondary electrons emitted in this manner was used to form an image for observation and evaluation by the above-described mapping projection system. As a result, the sample 22 negatively charged by irradiation with electrons from the hot electron source 41 was changed to a zero-charge state, i.e., to an equilibrium state by a neutralizing action of the nitrogen gas. If a material such as an insulating material is irradiated with an electron beam, the material tends to be positively charged. To avoid this, a hot electron source is used to change a surface of the material from a positively charged state through a zero-charge state to a negatively charged state by electron irradiation, but it is difficult to control such processing (neutralization). In the nitrogen gas, it is possible to prevent the progress of negative charge on the sample from being impeded by affinity to electrons. Further, a good image without any charge-up nor distortion was obtained even in peripheral portions having large image height or in regions made of insulating materials. When defect inspection on the wafer was performed by using this image, it was revealed that a rate of misinformation was remarkably reduced.

Example 2

The same process as that in Example 1 was performed at a gas pressure higher than the gas pressure 0.1 Pa in Example 1 by introducing more nitrogen gas. Because the gas molecules came more frequently into contact with the sample 22, electric charge on the surface of the sample 22 was removed and the sample surface was positively charged. At a gas pressure lower than 0.01 Pa, the wafer continued to be negatively charged. In either case, it was revealed that a good image without any distortion was not obtained.

Example 3

A halogen gas having higher affinity to electrons than nitrogen was introduced and the process in Example 1 was carried out. It was found that the time required for electric charge to be balanced on the surface of the sample 22 was reduced and that it was possible to enhance a throughput of inspection of a sample such as a wafer.

Example 4

Prior to irradiation of the sample 22 with the primary electron beam, the sample 22 was irradiated with electrons by using a carbon nanotube cold cathode source in place of the hot electron source 41 having such a hot filament as tungsten. In this case, it was found possible to irradiate, with a uniform current density distribution, a sample region larger than when the hot electron source having a hot-filament was used.

Figure 8:
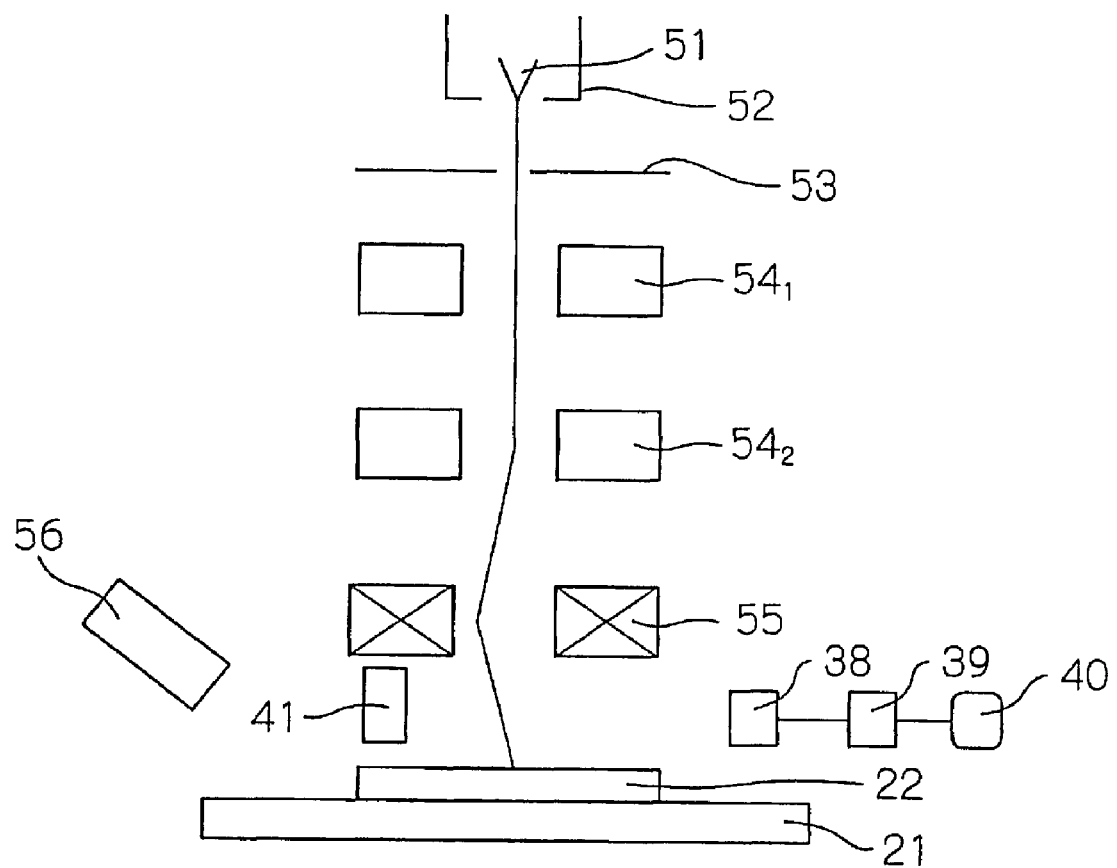
FIG. 8 is a diagram schematically showing the construction of still another embodiment of the present invention.

Referring now to FIG. 8, it schematically shows the construction of another embodiment of an electron beam apparatus according to the present invention. The electron beam apparatus is of a scanned electron beam type. After the sample 22 became balanced by the above-described method, the sample 22 is moved to a position just below a scanning electron beam. Electrons emitted from an electron gun 51 are accelerated by an anode 52, pass through an aperture 53 and electrostatic lenses 54, and 542 and irradiate the sample 22. During travel from the electron gun 51 to the sample 22, the electron beam is deflected by a scanning coil 55 and the electrostatic lens 542 and scans the surface of the sample 22 at a desired magnification. Secondary electrons, backscattered electrons or reflected electrons emitted from the sample 22 by electron beam irradiation are detected with a detector 56 such as a photomultiplier to obtain a two-dimensional image. The obtained image is used to conduct a die-by-die comparison or to compare image data with a data image for defect inspection.

Figure 9:
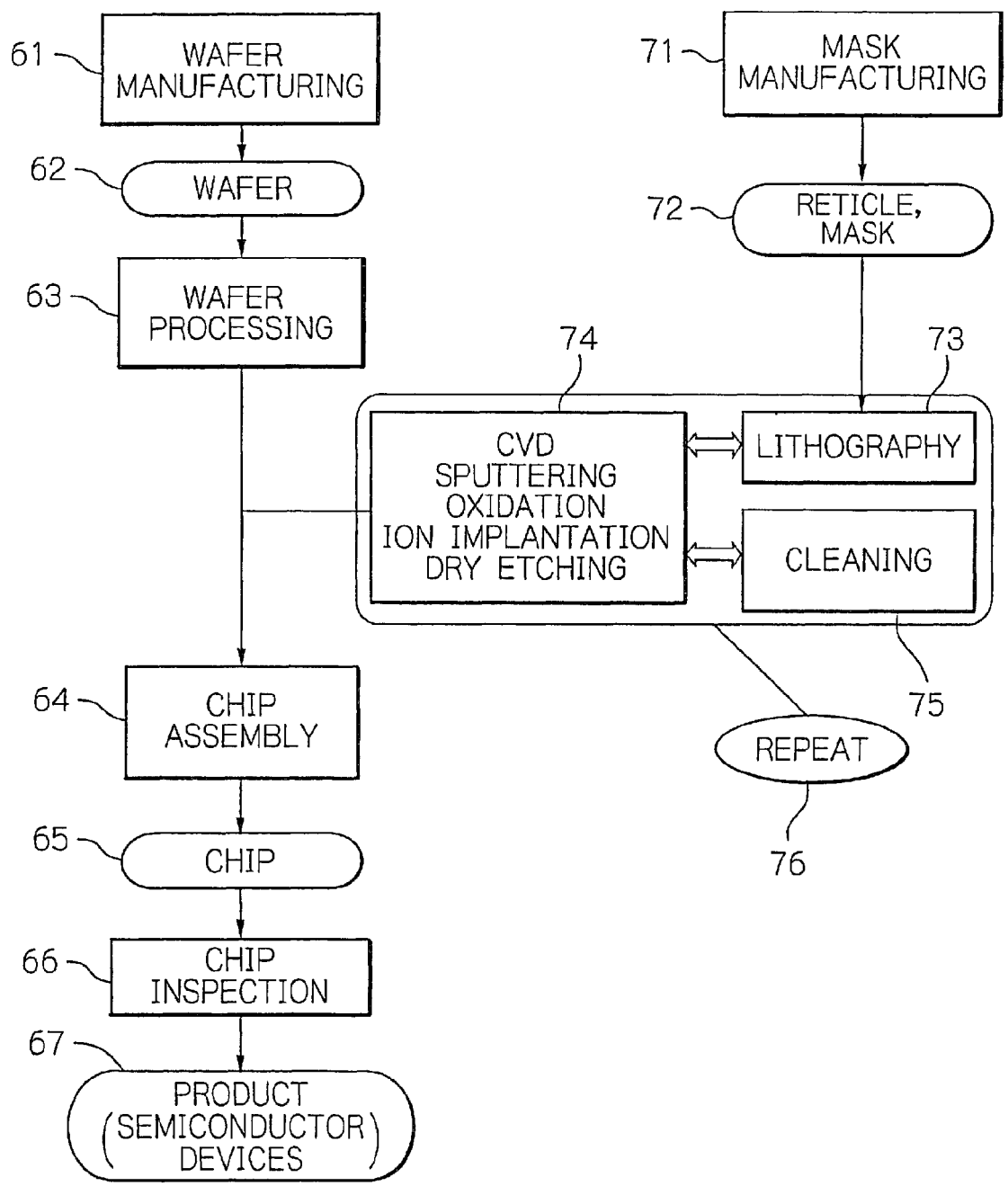
FIG. 9 is a flowchart showing an example of a semiconductor manufacturing method to which the mapping-projection-type electron beam apparatus in accordance with the present invention can be applied.

Now, a semiconductor device manufacturing method using an electron beam apparatus according to the present invention will be described. FIG. 9 is a flowchart showing an example of the manufacturing method, which includes the following main steps, each main step comprising several sub-steps:

(1) Step 61 of manufacturing or preparing a wafer 62;

(2) Mask manufacturing step 71 of manufacturing a mask (reticle) 72 used for exposure (or a mask preparing step of preparing a mask);

(3) Wafer processing step 63 of performing necessary processing on the wafer;

(4) Chip assembling step 64 of cutting out each chip formed on the wafer and making the chip operable; and (5) Chip inspecting step 66 of inspecting chips 65 produced in the chip assembling step 64.

Among the main steps, it is the wafer processing step 63 that exerts a decisive influence on the performance of the semiconductor device. In the wafer processing step, designed circuit patterns are successively laminated on the wafer and a multiplicity of chips operable as memory or MPU are formed. The wafer processing step 63 includes the following steps:

(a) a thin-film forming step (using CVD, sputtering or the like) of forming a dielectric thin film operable as an insulating layer as well as a metal thin film used to form wires or electrodes;

(b) an oxidation step of oxidizing thin film layers and a wafer substrate;

(c) a lithography step 73 of forming a pattern of a resist by using the mask (reticle) 72 for selectively processing the thin film layers and the wafer substrate;

(d) an ion/impurity implantation/diffusion step;

(e) a resist removal step; and (f) an inspection step of inspecting processed wafers.

It is noted that the wafer processing step 63 is repeatedly performed at times equal to the number of necessary layers to manufacture semiconductor devices capable of operation as designed.

Figure 10:
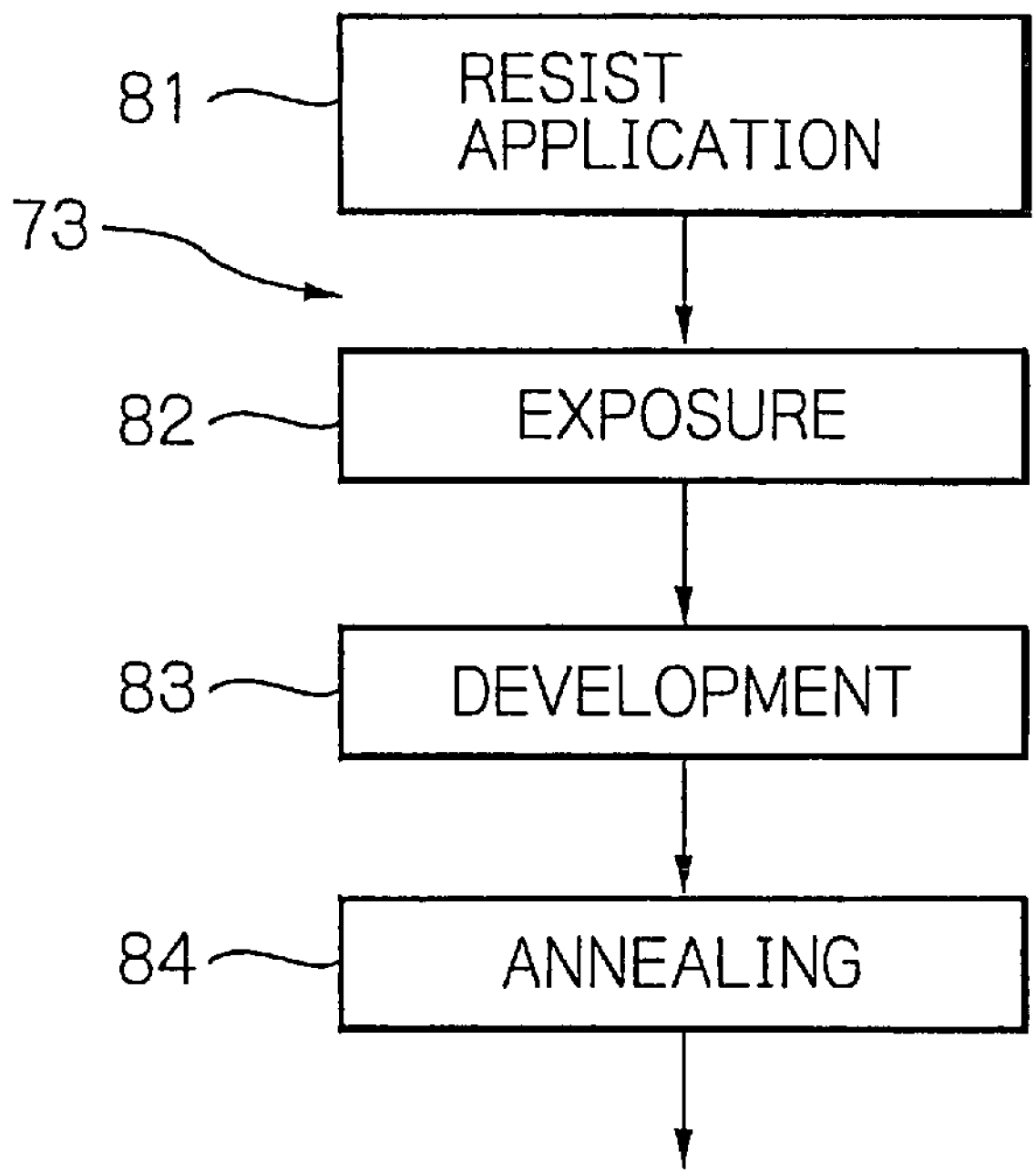
FIG. 10 is a flowchart showing a lithography step forming the heart of the wafer processing step shown in FIG. 9.

It is the lithography step 73 that forms the heart of the wafer processing step 63 shown in FIG. 9. FIG. 10 shows the following steps executed in the lithography step 73:

(a) a resist applying step 81 of coating, with a resist, the wafer on which the circuit patterns were formed in the preceding step;

(b) an exposure step 82 of exposing the resist;
(c) a development step 83 of obtaining a resist pattern by developing the exposed resist; and
(d) an annealing step 84 of stabilizing the developed resist pattern.

It is noted that the semiconductor device manufacturing process, the wafer processing step 63 and the lithography step 73 all described above are well-known and no further description thereof will be given here.

When defect inspection is performed by using an electron beam apparatus according to the present invention in the chip inspection step 66, a semiconductor device having fine patterns can be inspected at an improved throughput, all semiconductor devises can be inspected, the yield of products can be improved, and the shipping of defective products can be avoided.

INDUSTRIAL APPLICABILITY

As can be understood from the description heretofore, the present invention can make an electric potential on a sample surface uniform and detect reflected electrons emitted from the sample surface. Consequently, the present invention enables an emitted electron image having small aberration and distortion to be obtained. As a result, the present invention is noticeably advantageous in that reliable defect detection and image processing can be achieved.

The invention claimed is:

1. A mapping-projection-type electron beam apparatus for observing and/or evaluating a surface of a sample by irradiating the sample with a primary electron beam and causing reflected electrons from the sample to form an image on a detector, said apparatus comprising:
    an electron-bombardment-type detector including an electron impact-type CCD or an electron impact-type TDI as said detector for detecting the reflected electrons,
    wherein said detector selectively detects the reflected electrons on the basis of an energy difference between the reflected electrons and secondary electrons emitted from the sample.

2. An electron beam apparatus as claimed in claim 1, further comprising an image processing mechanism for processing the output of said electron-bombardment-type detector to produce an image for evaluation and inspection, wherein a gain of said electron-bombardment-type detector and an amount of exposure of the image for evaluation and inspection are adjusted by changing the energy of the primary electron beam incident on the sample.

3. An electron beam apparatus as claimed in claim 1, wherein the electron-bombardment-type detector has a multiplication gain which is a function of incident energy of the electrons.

4. An electron beam apparatus as claimed in claim 1, 2 or 3, wherein the energy of the primary electron beam incident on the sample is 2 to 4 keV thereby charging the surface of the sample negatively so as to reduce image distortion due to charge-up on the surface of the sample.

5. An electron beam apparatus as claimed in claim 1, 2 or 3, wherein the landing energy of the primary electron beam on the sample is set to 0.2 to 4.0 keV thereby improving an S/N ratio by detecting said reflected electrons and backscattered electrons.

6. An electron beam apparatus as claimed in claim 1, 2 or 3, further comprising cooling means for cooling the electron-bombardment-type electron impact type detector to reduce heat generated due to electron bombardment.

7. A method of manufacturing a semiconductor device, comprising a step of evaluating a wafer in the course of processing, by using the electron beam apparatus according to claim 1, 2 or 3.

8. An electron beam apparatus as claimed in claim 1, wherein the detector selectively detects the reflected electrons by using a multiplication gain of the electron-bombardment-type detector.

* * * * *

UNITED STATES PATENT AND TRADEMARK OFFICE
CERTIFICATE OF CORRECTION

PATENT NO. : 8,124,933 B2
APPLICATION NO. : 12/538416
DATED : February 28, 2012
INVENTOR(S) : Kenji Watanabe et al.

Page 1 of 1

It is certified that error appears in the above-identified patent and that said Letters Patent is hereby corrected as shown below:

Title Page, In item (75), Inventors:
Change the name of the sixth inventor
"Nobuhara Noji,"

To be

--Nobuharu Noji,--

Title Page, In item (62), Related U.S. Application Data:
After "Pat. No. 7,592,586"

Insert

--, filed as application No. PCT/JP2004/000711 on January 27, 2004--

Signed and Sealed this
Third Day of July, 2012

David J. Kappos
*Director of the United States Patent and Trademark Office*